(12) United States Patent
Benoit et al.

(10) Patent No.: US 6,451,297 B1
(45) Date of Patent: Sep. 17, 2002

(54) HAIR AND/OR BODY CARE PRODUCT FOR HUMAN BEINGS AND ANIMALS

(76) Inventors: Jean-Pierre Benoit, 145, rue Victor Hugo, 14800 Deauville (FR); Elisabeth Bac, 145, rue Victor Hugo, 14800 Deauville (FR)

( * ) Notice: Subject to any disclaimer, the term of this patent is extended or adjusted under 35 U.S.C. 154(b) by 0 days.

(21) Appl. No.: 09/555,460

(22) PCT Filed: Dec. 1, 1998

(86) PCT No.: PCT/FR98/02581

§ 371 (c)(1),
(2), (4) Date: May 30, 2000

(87) PCT Pub. No.: WO99/27899

PCT Pub. Date: Jun. 10, 1999

(30) Foreign Application Priority Data

Dec. 2, 1997 (FR) .............................................. 97 15173

(51) Int. Cl.⁷ .............................. A61K 7/06; A61K 7/08; A61K 31/74; A61K 9/14

(52) U.S. Cl. ................. 424/70.1; 424/70.19; 424/70.21; 424/70.22; 424/70.27; 424/70.31; 424/74; 424/78.02; 424/489

(58) Field of Search .............................. 424/70.1, 70.19, 424/70.21, 70.22, 70.27, 70.31, 74, 78.02, 489

(56) References Cited

U.S. PATENT DOCUMENTS

| | | | |
|---|---|---|---|
| 4,012,341 A | | 3/1977 | Orshitzer et al. |
| 4,330,438 A | * | 5/1982 | Dierassi et al. ............. 252/552 |
| 5,990,058 A | | 11/1999 | Bac et al. |

FOREIGN PATENT DOCUMENTS

| | | |
|---|---|---|
| DE | 27 52 320 | 6/1978 |
| DE | 44 43 644 | 6/1996 |
| EP | 0 330 425 | 2/1989 |
| EP | 0 330 435 A2 * | 8/1989 |
| FR | 2 555 441 | 5/1985 |
| GB | 1 581 377 | 11/1977 |
| WO | 92 09260 | 6/1992 |
| WO | 92/09266 * | 6/1992 |
| WO | WO93/07245 | 4/1993 |
| WO | WO96/16922 | 6/1996 |

OTHER PUBLICATIONS

Abstract in English of DE 4 214 480.

Translation in English relevant passages of <<Science des traitements capillaires>>, Charles Zviak, Ed. Masson, 1988, pp 73 & 78.

Abstract in English of FR 2 555 441.

Base De Donnees "Chemical Abstracts" (Serveur: STN), Abr. 117:97 987, Colombus, OH, USA; & JP 04 049 224 A (Kao K.K.) XP002074250.

* cited by examiner

*Primary Examiner*—Thurman K. Page
*Assistant Examiner*—S. Tran
(74) *Attorney, Agent, or Firm*—Henderson & Sturm LLP

(57) ABSTRACT

The invention concerns a hair and/or body care product for humans or animals, in the form of a powder having a granulometry of 30 to 500 microns, applicable directly to the wet hair and/or the body and comprising, percentages being expressed as percentages by weight relative to the total weight of the powder, less than 40% of at least one surfactant, and from 1 to 12% of at least one perfume, the percentage being made up to 100% by one or more products selected from the group consisting of sugars, starches, celluloses, polyols, proteins, amino acids, perfumes, colourings, antioxidants, plant substances, seaweed, vitamins, essential oils and mineral fillers.

18 Claims, No Drawings

HAIR AND/OR BODY CARE PRODUCT FOR HUMAN BEINGS AND ANIMALS

This application is a 371 of PCT/FR98/02581 filed Dec. 1, 1998.

The invention relates to a hair and/or body care product for humans and animals, in the form of a powder applicable directly to the hair or the body.

It also relates to the process for manufacturing this product.

The product according to the present invention may be used as a shampoo for washing hair and/or the body, as a hair detangling product, as a "conditioning" product or also as an exfoliant for the body.

Several forms of shampoo are known in the prior art. The conventional form is liquid shampoo. Nevertheless, shampoos also exist in the form of gels, creams or aerosol mousses.

Shampoos in solid form have also been proposed in the prior art. However, these "solid" shampoos are always in the form of shaped products, for example bars, pellets or tablets. Reference may thus be made to the following patents or patent applications: U.S. Pat. No. 4 012 341, WO 93/07245, EP 0 330 435.

French patent application FR 95 08265, filed by the inventors, may also be cited, since it describes a hair care product for humans or a hair treatment product for animals in the form of tablets which have a rather short disintegrating time on the hair. This product is very easy to transport and exhibits good storage stability, even in a damp atmosphere. However, this tablet-form presentation has certain disadvantages. In particular, it has been noted in use that the tablets do not disintegrate wholly satisfactorily in the case of thick hair. These problems seem substantially to stem from the fact that the hair has to be very thoroughly wetted for the tablet to produce acceptable results.

However, in any case, it was never seriously intended in the prior art that a shampoo in powder-form should be applicable directly to the hair or the body, since it was inconceivable that such an application could provide satisfactory results.

It is of course true that powder-form shampoos have already been proposed, but it should be emphasised that they were always designed to be dissolved before use, which, as far as utilisation is concerned, puts them in the same category as a liquid shampoo.

Charles Zviak, in "Science des traitements capillaires" (Masson, 1988), thus described powder-form shampoos to be dissolved at the time of use in order to obtain a liquid shampoo. He pointed out in this publication that powder-form shampoos to be dissolved at the time of use are used less and less, despite the fact that they constitute the cheapest form. According to Zviak, this is because they are not very convenient to use. To this may be added the difficulty of adding high quality ingredients to a pulverulent product which has to dissolve very easily at the time of use.

As far as the inventors are aware, the only document which mentions use of a powder-form shampoo is patent application DE 4214480. This document provides a very brief description of a process for using a hair shampoo reduced to a powder, this process being characterised in that a shampoo reduced to a powder by drying is sprinkled on the wet hair and mixes with the water to produce a normal shampoo.

However, from reading the six lines which comprise this patent application, it is clear that it relates to a conventional liquid shampoo formulation which has been dried to convert it into powder form.

Due to this process for drying liquid shampoo, the resultant powder obviously contains only the active ingredient, that is to say substantially surfactants.

Given this extremely high active ingredient content (actually approaching 100%), the inventor of the above-stated German patent application could indeed expect to achieve an acceptable result from applying the dehydrated liquid shampoo directly to the hair. However, it should be noted that the description, which could not be any briefer, of this patent application does not contain any details as to composition or any evaluation of the results obtained.

The fact remains that the powder in question, obtained therefore by drying liquid shampoo, cannot on any account be economically viable, nor provide the advantages which will be described below in relation to the product according to the invention.

The latter is characterised in that it is in the form of a powder which contains at most only 40% active ingredients, that is to say washing products or lather-producing products.

For this reason, the powder-form product according to the present invention is capable of comprising other products such as perfumes, colourings, antioxidants, vitamins, essential oils, plant substances, seaweed, these being in markedly greater quantities than in a normal liquid shampoo or in the powder obtained by drying a liquid shampoo, as described in patent application DE 4214480.

Surprisingly and unexpectedly, the hair and/or body care product in powder form according to the present invention has very satisfactory washing and lather-forming capacities, despite the fact that the powder contains a percentage of active ingredients considerably lower than the only powder-form shampoo mentioned in the prior art.

The hair and/or body care product for humans and animals which constitutes the subject matter of the present invention is characterised in that it is in the form of a powder applicable directly to the hair and/or the body and in that it comprises less than 40%, preferably less than 35%, and still more preferably less than 30%, of at least one surfactant, these percentages being expressed as percentages by weight relative to the total weight of the powder. The percentage is made up to 100% by one or more products selected from the group comprising sugars, starches, celluloses, polyols, proteins, amino acids, perfumes, colourings, antioxidants, plant substances, seaweed, vitamins, essential oils and mineral fillers.

The surfactants used in the hair and/or body care product according to the invention may be surfactants of the anionic, cationic, nonionic or amphoteric type.

Anionic surfactants are preferred, owing to their good washing and lather-forming capacity. Examples which may be cited are alkyl sulfates, such as lauryl sulfates, alkyl and aryl sulfonates, olefin sulfonates and secondary alkyl sulfonates, alkyl ether sulfates and the esters of sulfosuccinic acid.

Use is preferably made of the sodium lauryl sulfate sold under the brand name TEXAPON K 1296, the disodium cocamido MEA sulfosuccinate sold under the brand name REWOPOL SBC 212P, and the fatty acid methyltaurides sold by HOECHST.

Cationic surfactants are most particularly suitable for specific applications such as the treatment of severely damaged hair and/or as detangling products for hair.

The product preferably used is sold by HERCULES under the brand name N HANCE 3196.

Of the nonionic surfactants, most exhibit the disadvantage of having only a poor lather-forming capacity. There are exceptions, however, examples of these nonionic surfactants which may be used within the context of the present invention being polysorbates, and polyglycerides and polyethoxylates of fatty alcohols.

The product according to the present invention preferably comprises a decyl polyglucoside nonionic surfactant, such as that sold under the brand name ORAMIX SP100.

Finally, amphoteric surfactants may also be used in the product according to the invention, since they have a good lather-forming capacity and are additionally very gentle on the hair. The amphoteric surfactants preferred within the context of the invention are derivatives of betaine. The product sold by GOLDSCHMIDT under the brand name TEGOBETAINE CKD is preferably used.

The hair and/or body care product according to the invention may also comprise a surfactant for increasing the lather-forming capacity ("foaming agent"). Copra fatty acid monoethanolamide, sold under the brand name COMPERLAN 100 is preferably used.

Examples which may be cited of sugars which may be included in the product according to the invention are glucose, glucose syrups, mannose, fructose, sucrose, maltose and maltose syrups, lactose, maltodextrins.

Starches suitable for use as fillers in the hair and/or body care product according to the present invention comprise potato starch and wheat, corn and rice starch.

Examples of polyols which may be cited are sorbitol, mannitol, lactitol, maltitol and in particular the products sold under the brand names NEOSORB P 60, NEOSORB P 100 T or MALTISORB P 90.

Examples which may be cited of proteins and amino acids suitable for inclusion in the hair and/or body care product according to the present invention are milk proteins, including caseinates, vegetable proteins such as wheat or soya proteins, keratin, in particular that sold under the brand name MONTEINE WKHP, cysteine, methionine. The formulation may also include products such as soya lecithin.

According to a preferred embodiment of the invention, the granulometry of the powder is between approximately 30 and approximately 500 microns, preferably between 60 and 300 microns, and still more preferably between 60 and 150 microns.

The powder-form hair and/or body care product according to the present invention may comprise approximately 0.3 to 12% perfume, optionally encapsulated or applied to a support, the percentages being expressed as percentages by weight relative to the total weight of the powder. The perfume content is preferably between 1 and 8%, and still more preferably between 2 and 6%. This possibility of including such a high percentage of perfume in the product according to the invention constitutes a decisive advantage of the present invention.

The powder-form hair and/or body care product according to the invention may also comprise vitamins, colourings, treatment proteins, encapsulated essential oils, depending on the specific requirements for the product.

Vitamins which may be added are vitamins B2, B5 and B6, vitamin PP and vitamin C.

The powder-form hair and/or body care product according to the invention may advantageously be packaged in single-dose form, in individual amounts of 2 to 10 g, such packaging being most particularly suitable for travel and sports products or those supplied by hotels.

The powder-form hair and/or body care product constituting the subject matter of the present invention produces a rich lather and also has a very pleasant exfoliating effect when used to wash the body.

The invention also provides a process for preparing the powder-form hair and/or body care product.

Said process comprises the following stages:

the ingredients to be included in the powder are selected;

where applicable, the volatile ingredients or those sensitive to light or heat, such as perfumes, essential oils, vitamins, are encapsulated or applied to a support;

the various ingredients are mixed intimately;

the mixture is optionally pulverised, and then screened to arrive at the selected granulometry;

the product is packaged.

Maltodextrins, liposomes or cyclodextrins are advantageously used for encapsulation or application to a support of the sensitive ingredients. Examples of suitable cyclodextrins are the products sold by ROQUETTE FRERES under the brand name KLEPTOSE.

Mixing is performed using methods known per se, such as a planetary mixer.

Mixing may be performed at a temperature between 5° C. and 25° C. Mixing is preferably performed at ambient temperature.

The product may be packaged in sachets or tubes, for example.

A great advantage of this simple process for preparing the product according to the invention is that it is easily possible to modify the contents of the powder, thereby adapting it to the specific needs of consumers.

The invention will be better understood from the following Example, provided purely by way of illustration.

EXAMPLE

| A powder-form hair care product having the following composition is prepared by dry mixing of the various constituents at a temperature of approximately 20° C.: | |
|---|---|
| pulverulent nonionic surfactant, brand name ORAMIX SP100, sold by SEPIC | 1.00% |
| pulverulent anionic surfactant, brand name REWOPOL SBC 212P, sold by WITCO | 9.00% |
| pulverulent anionic surfactant, brand name TEXAPON K 1296, sold by HENKEL | 11.00% |
| lather-enhancer, brand name COMPERLAN 100, sold by HENKEL | 1.00% |
| pulverulent cationic polymer, brand name N HANCE 3196, sold by HERCULES | 2.20% |
| wheat fibre hydrolysate, brand name SOFABRAN F 146 (BLE), sold by SOFALIA | 0.90% |
| keratin, brand name MONTEINE W KHP, sold by SEPPIC | 0.20% |
| sorbitol, brand name NEOSORB P60 and NEOSORB P100T, sold by ROQUETTE FRERES NEOSORB P100T | 56.00% |
| MALTISORB P90, sold by ROQUETTE FRERES | 13.64% |
| Perfume | 5.00% |
| Colouring | 0.06% |

The product is then packaged in tubes, each containing approximately 5 g.

10 people, 6 women and 4 men, tested the product. Although it lathers more slowly than a conventional liquid shampoo, it was unanimously recognised as being very satisfactory.

The testers liked the softness and sheen of their hair after testing the shampoo and emphasised that it was extremely pleasant to use owing to the perfume which develops during use and remains on the hair. The testers were also unanimous in their view that presentation of the product in powder form did not pose any problem at the time of application to the hair and that, on the contrary, the product was very convenient to use.

What is claimed is:

1. A hair and/or body care product for humans or animals, in the form. of a powder having a granulometry of 30 to 500 microns, applicable directly to the wet hair and/or the body and comprising, percentages being expressed as percentages by weight relative to the total weight of the powder, less than 40% of at least one surfactant, and from 1 to 12% of at least one perfume, the percentage being made up to 100% by one or more products selected from the group consisting of sugars, starches, celluloses, polyols, proteins, amino acids, perfumes, colourings, antioxidants, plant substances, seaweed, vitamins, essential oils and mineral fillers.

2. The hair and/or body care product according to claim 1 containing less than 35% of at the least one surfactant.

3. The hair and/or body care product according to claim 2 containing less than 30% of at the least one surfactant.

4. The hair and/or body care product according to claim 1, wherein the surfactant(s) are selected from the group consisting of anionic, nonionic, cationic and amphoteric surfactants.

5. The hair and/or body care product according to claim 1, wherein the anionic surfactants are selected from the group comprising alkyl sulfates, alkyl and aryl sulfonates, olefin sulfonates, alkyl ether sulfates and the esters of sulfosuccinic acid.

6. The hair and/or body care product according to claim 5, wherein the anionic surfactants is sodium lauryl sulfate.

7. The hair and/or body care product according to claim 1, wherein the nonionic surfactant is a decyl polyglucoside.

8. The hair and/or body care product according to claim 1, wherein the amphoteric surfactant is a betaine derivative.

9. The hair and/or body care product according to claim 1, comprising an agent increasing the lather-forming capacity of said product.

10. The hair and/or body care product according to claim 9, wherein the agent increasing the lather-forming capacity of said product is copra fatty acid monoethanolamide.

11. The hair and/or body care product according to claim 1, comprising a cationic surfactant as a hair detangling product.

12. The hair and/or body care product according to claim 1, comprising a cationic polymer as a hair detangling product.

13. The hair and/or body care product according to claim 1, wherein the powder has a granulometry of 60 to 300 microns.

14. The hair and/or body care product according to claim 13, wherein the powder has a granulometry of 60 to 150 microns.

15. The hair and/or body care product according to claim 1, comprising at least one perfume, with a content of between 1 and 8%.

16. The hair and/or body care product according to claim 15, comprising at least one perfume, with a content of between 2 and 6%.

17. The hair and/or body care product according to claim 1, packaged in single dose form.

18. A process for the production of the product according to claim 1, comprising the following steps:

the ingredients to be included in the powder are selected;

where applicable, the volatile ingredients or those sensitive to light or heat, selected from the group consisting of perfumes, essential oils, vitamins, are encapsulated or applied to a support;

the various ingredients are mixed intimately;

the mixture is optionally pulverised, and then screened to arrive at the selected granulometry of from 30 to 500 microns;

the product is packaged.

* * * * *